United States Patent [19]

Dowd et al.

[11] Patent Number: 5,149,525
[45] Date of Patent: * Sep. 22, 1992

[54] ORGANOPHOSPHORUS INSECTICIDES AS SYNERGIZICIDES FOR CARPOPHILUS SPP. PHEROMONES

[75] Inventors: Patrick F. Dowd, Peoria; Robert J. Bartelt, East Peoria, both of Ill.

[73] Assignee: The United States of America, as represented by the Secretary of Agriculture, Washington, D.C.

[*] Notice: The portion of the term of this patent subsequent to Apr. 16, 2008 has been disclaimed.

[21] Appl. No.: 610,903

[22] Filed: Nov. 9, 1990

Related U.S. Application Data

[63] Continuation-in-part of Ser. No. 387,555, Jul. 31, 1989, Pat. No. 5,008,478, which is a continuation-in-part of Ser. No. 275,863, Nov. 25, 1988, Pat. No. 5,011,683.

[51] Int. Cl.$^5$ ............................................. A01N 25/00
[52] U.S. Cl. ............................................. 424/84
[58] Field of Search ...................................... 424/84

[56] References Cited

U.S. PATENT DOCUMENTS

| | | | |
|---|---|---|---|
| 4,272,520 | 6/1981 | Kydonieus et al. | 424/84 |
| 4,734,281 | 3/1988 | Yamamoto et al. | 525/84 |
| 4,853,217 | 8/1989 | Francke | 424/84 |
| 5,008,478 | 4/1991 | Bartelt et al. | |
| 5,011,683 | 4/1991 | Bartelt et al. | |

OTHER PUBLICATIONS

Philips' CA:69: 87241a.
J. M. Smilanick et al., "Attraction of Carpophilus Spp. (Coleoptera: Nitidulidae) to Volatile Compounds Present in Figs," J. Chem. Ecol. 4(6): 701–707 (1978).
D. J. Pree, "Control of *Glischrochilus quadrisignatus* (Say) Coleoptera: Nitidulidae), a Pest of Fruit and Vegetables in Southwestern Ontario," Proc. Entomol. Soc. Ontario 99: 60–64 (1968).
R. L. Metcalf, "Plant Volatiles as Insect Attractants," CRC Critical Reviews in Plant Sciences 5(3): 251–301 (1987).
R. L. Metcalf et al., "Molecular Parameters and Olfaction in the Oriental Fruit Fly *Dacus dorsalis*," Proc. Natl. Acad. Sci. USA 78(7): 4007–4010 (Jul., 1981).

*Primary Examiner*—Frederick E. Waddell
*Assistant Examiner*—Russell Travers
*Attorney, Agent, or Firm*—Silverstein, M. Howard; Randall E. Deck; John D. Fado

[57] ABSTRACT

The attractiveness of the male-produced aggregation pheromones from nitidulid beetles is greatly enhanced by certain organophosphorus insecticides. Combinations of pheromone and insecticide typically attract substantially more beetles than the pheromone alone, and the combinations afford the advantage of both attracting and killing the beetles.

22 Claims, No Drawings

ORGANOPHOSPHORUS INSECTICIDES AS SYNERGIZICIDES FOR CARPOPHILUS SPP. PHEROMONES

CROSS-REFERENCES TO RELATED APPLICATIONS

This application is a continuation-in-part of application Ser. No. 07/387,555, filed Jul. 31, 1989, now U.S. Pat. No. 5,008,478, which is a continuation-in-part of application Ser. No. 275,863, filed Nov. 25, 1988, now U.S. Pat. No. 5,011,683.

BACKGROUND OF THE INVENTION

1. Field of the Invention

The nitidulid beetles, such as *Carpophilus freemani, C. hemipterus*, and *C. lugubris*, are significant pests of fruits and vegetables, as well as vectors of pathogens to trees and vectors of mycotoxin-producing fungi to corn. This invention relates to organophosphorus insecticides that synergistically increase the attractancy of pheromones from these insects. Thus, these organophosphorus compounds not only kill the insects but they also extend the life of pheromone-containing baits and decrease the amount of pheromone needed.

2. Description of the Prior Art

Insect-produced volatiles (e.g., pheromones) and host plant odors (e.g., kairomones) may facilitate location of conspecifics for mating and orientation to acceptable host plants for feeding and oviposition. It is known that in several, but not all, insect species (e.g., bark beetles) pheromones and a few specific plant odors, such as monoterpenes, may act in synergy, each enhancing the attraction of the other [Borden, In Insect Communication, T. Lewis, ed., Academic Press, New York, p. 123 (1984)].

*Carpophilus hemipterus* (L.) (Coleoptera: Nitidulidae) is a worldwide pest attacking agricultural commodities such as ripe and dried fruit, corn, wheat, oats, rice, beans, nuts, peanuts, cotton seed, copra, spices, sugar, honey, and other materials [Hinton, A Monograph of the Beetles Associated with Stored Products, Jarrold and Sons, Norwich, U.K., 443 pp. (1945)]. It is also able to vector microorganisms responsible for the souring of figs (Hinton, supra) and fungi which contaminate corn and produce mycotoxins [Wicklow et al., In NC-151, 1987: Annual Progress Reports from Participating Laboratories, pp. 31–32 (1988)].

The dusky sap beetle, *Carpophilus lugubris* Murray (Coleoptera: Nitidulidae) is distributed from Brazil through Central America [Parsons, Harvard Univ. Museum Comp. Zool. Bull. 92: 121–278 (1943)] and probably throughout the United States [Sanford, Observations on the biology and control of the dusky sap beetle, *Carpophilus lugubris* Murray, infesting sweet corn in Illinois, Univ. of Illinois, Urbana, 54 pp. (1958)]. It is found in ripe and decomposing fruit and vegetables [Sanford et al., Proc. North Central Br. Entomol. Soc. Am. 18: 39–43 (1963)], trees infected with oak wilt [Dorsey et al., Plant Dis. Rep. 37: 419–420 (1953); Norris, Plant Dis. Rep. 37: 417–418 (1953)], and poultry manure [Pfeiffer et al., Environ. Entomol. 9: 21–28 (1980)]. It is probably most important as a pest of sweet corn [Connell, Nitidulidae of Delaware, Univ. of Delaware Agric. Exper. Sta. Tech. Bull. #318, 67 pp. (1956); Sanford, supra; Connell, J. Econ. Entomol. 68: 279–280 (1975); Tamaki et al., J. Entomol. Soc. Brit. Columbia 79: 3–8 (1982)], and can cause large amounts of corn to be rejected at canneries [Luckman et al., Proc. North Central Br. Entomol. Soc. Am. 14: 81–82 (1959)]. In addition, it appears to be a vector of oak wilt [Dorsey et al., supra; Norris, supra; Appel, J. Econ. Entomol. 79: 1276–1279 (1986)], and mycotoxin-producing fungi that contaminate corn [Wicklow et al., supra]. Although tight-husked corn can provide some control, this may be defeated when corn earworms or other insects provide entry holes [Connell, supra (1956); Tamaki et al., supra]. However, in many cases these insects are able to enter the ears without assistance [Connell, supra (1956); Tamaki et al., supra]. The loose-husked varieties of dent (field) corn adopted in association with the use of mechanical harvesting promote ready entry sites for these insects [Connell, supra (1956)].

*Carpophilus freemani* Dobson infests sweet corn [Sanford et al., supra] and corn seed and corn meal [Connell, supra (1975)]. It is a principal pest of figs [Smilanick et al., Proc. Calif. Fig Inst. Res. Meet. 1976: 27–41 (1976)] and the principal vector of Ceratocystis canker of stone fruits including almonds, prunes, peaches, and apricots [Moller et al., Phytopathology 59: 938–942 (1969)].

Field traps have been used to monitor or attempt to control these and other nitidulid species, and much research has gone into trap baits. Fermenting fig paste has been used as a trap bait for *C. hemipterus* [Obenauf et al., Proc. Calif. Fig Inst. Res. 1976: 61–94 (1976)]. Smilanick et al., [J. Chem. Ecol. 4: 701–707 (1978)] determined that a 1:1:1 mixture of acetaldehyde, ethyl acetate, and ethanol was an even more effective bait for *C. hemipterus* than fig paste, but trap catches were still relatively small, given the huge beetle populations. Due to the low activity of 16 other host volatiles tested, Smilanick et al. [supra (1978)] concluded that *C. hemipterus* "appears to use a restricted number of olfactory stimuli to locate suitable hosts." Previously reported methods of monitoring *C. lugubris* have been of limited effectiveness. It is well known that these insects can be attracted by fermenting baits [Luckman, supra]. Specific methods include using freshly sawn oak or maple blocks in combination with vinegar and fungi [Neel et al., J. Econ. Entomol. 60: 1104–1109 (1967); Dorsey et al., J. Econ. Entomol. 49: 219–230 (1956)]. However, the attractiveness of these baits varies over time due to changes in fermentative activity [Neel et al., supra]. Previously reported methods of attracting *C. freemani* are also of limited effectiveness. The only reported method specifically describing *C. freemani* attraction is that of Smilanick et al. [supra (1978)]. The response of *C. freemani* to Smilanick's 3-component mixture appeared to be relatively poor compared to that of *C. hemipterus*, and not significantly different from fig paste or controls. Alm et al. [J. Econ. Entomol. 78: 839–843 (1985); ibid. 79: 654–658 (1986)] demonstrated that esters such as propyl propionate and butyl acetate were effective baits for *Glischrochilus quadrisignatus*, another economically important nitidulid, but did not compete with banana. In nature, these chemicals exist in the host plant, are produced by microorganisms which have established on the plants, or both.

SUMMARY OF THE INVENTION

We have now surprisingly found that organophosphorus insecticides are effective synergizicides for nitidulid pheromones, synergistically increasing the attractancy of the pheromones in addition to killing the insects upon exposure thereto.

In accordance with this discovery, it is an object of the invention to provide new compositions for controlling insects.

A further object of the invention is to provide new means to synergize the effect of insect pheromones.

Other objects and advantages of the invention will become obvious from the ensuing description.

DETAILED DESCRIPTION OF THE INVENTION

The importance of olfaction in the behavior of insects is well known. Insect-produced volatiles, e.g., pheromones, and host plant odors may facilitate location of conspecifics for mating and orientation to acceptable host plants for feeding and oviposition. Pheromones that are attractive alone may have their activity enhanced or synergized by odors that show little or no attraction when presented alone.

With the identification of aggregation pheromones of nitidulid beetles by Bartelt et al., (U.S. patent application Ser. No. 387,555, filed Jul. 31, 1989, "Aggregation Pheromones of the Nitidulid Beetles *Carpophilus hemipterus, Carpophilus lugubris* and *Carpophilus freemani*", the contents of which are herein incorporated by reference), a tool became available to monitor beetle populations for directing insecticide applications and evaluating control measures. The pheromones might also be potentially used to control pest populations by employing large numbers of traps (trap-out strategy). However, the pheromones currently lack a synergizicide, which both increases the attractancy of the pheromones and also kills the insects.

According to this invention, there is provided a composition for controlling nitidulid beetles which includes a pheromone attractant for nitidulid beetles and an amount of an organophosphorus insecticide effective to synergizicidally attract the nitidulids.

A synergist is herein defined as a material that enhances the activity of other materials, so that the overall activity of the mixture is greater than the sum of the individual components. A synergizicide is herein defined as an insecticide that is a synergist.

Without desiring to be bound by any particular theory of operation, it is believed that the organophosphorus insecticides act as synergizicides by stimulating certain specific olfactory cells in the insect antenna.

An effective synergizicide for an insect pheromone provides a variety of advantages beyond the apparent utility of functioning as an insecticide for the control of the insect population. Such a synergizicide for an aggregation pheromone reduces the amount of pheromone needed, and reduces or eliminates the need for other chemicals to be added as synergists for the pheromone, thereby reducing the cost of insect control. Also, because many inappropriate insecticides may repel the object insects, a synergizicide also ensures that insects will find the formulation attractive and will not be repelled by it. A synergizicide may even further enhance the overall attractiveness of the formulation by inhibiting catabolic enzymes that can break down an analogous natural attractant, or by acting as an irreversibly-binding agonist at the receptor itself. The net result in either of these possibilities is that the receptor is stimulated more often (and insect attractancy enhanced) than it would be by the pheromone or natural attractant alone.

The synergizicide-pheromone compositions encompassed herein are effective in controlling a variety of insects. Without desiring to be limited thereto, pests of particular interest for treatment according to the invention are agronomically important nitidulids, including Carpophilus, Glischrochilus or Colopterus species, and especially *Carpophilus hemipterus, C. lugubris*, and *C. freemani*.

Suitable pheromones for use in the invention include aggregation pheromones exhibiting an attractant response for nitidulid beetles. Preferred pheromones include, but are not limited to, those pheromones disclosed by Bartelt et al. (Ser. No. 387,555) which may be represented by the general formula:

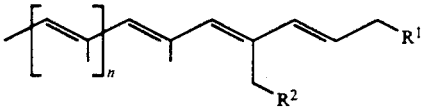

wherein $R^1$ and $R^2$ are independently selected from hydrogen or lower alkyl, and n is zero or one. Especially preferred are those pheromones wherein: $R^1$ is hydrogen, $R^2$ is hydrogen, and n is one; $R^1$ is methyl, $R^2$ is hydrogen, and n is one; $R^1$ is hydrogen, $R^2$ is methyl, and n is one; $R^1$ is methyl, $R^2$ is methyl, and n is one; $R^1$ is ethyl, $R^2$ is hydrogen, and n is one; and $R^1$ is methyl, $R^2$ is methyl, and n is zero. The pheromones of this invention may be used as a crude extract of Carpophilus sp. beetles or in substantially purified form either isolated from the natural source or chemically synthesized.

Suitable organophosphorus insecticides contemplated as components of the invention compositions are those effective as synergizicides for the aggregation pheromones. Exemplary organophosphorus insecticides include but are not limited to dichlorvos (2,2-dichlorovinyl dimethyl phosphate (I)), thiometon (S-2-ethylthioethyl O,O-dimethyl phosphorodithioate), naled (1,2-dibromo-2,2-dichloroethyl dimethyl phosphate(I)), parathion (O,O-diethyl O-4-nitrophenyl phosphorothioate), and IBP (S-benzyl O,O-di-isopropyl phosphorothioate (I)). It is anticipated that other organophosphorous insecticides can also be used. In this regard, organophosphorous insecticides are identified by the formula:

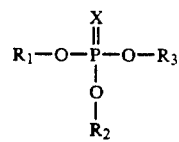

wherein $R_1$ and $R_2$ are generally methyl or ethyl, $R_3$ is a variable hydrocarbon, and X is O or S. Other particularly suitable organophosphorous insecticides would include those having $R_3$ groups which are: 1) straight chain hydrocarbons, especially those having a chain length of about $C_1$–$C_8$; or 2) branched chain hydrocarbons having no more than about one methyl branch; or 3) aromatic hydrocarbons (e.g., benzyl). Insecticides from groups (1) and (2) above are especially effective synergizicides for the pheromones of *Carpophilus hemipterus* and *C. freemani*, while insecticides from group (3) are especially effective synergizicides for the pheromones of *C. lugubris*.

The potency of these synergizicide-pheromone compositions dictates that they be applied in conjunction with a suitable inert carrier or vehicle as known in the art. Of particular interest are those which are agronomically acceptable. Alcohols, hydrocarbons, halogenated hydrocarbons, glycols, ketones, esters, and aqueous mixtures, and solid carriers such as clays, cellulose, rubber, or synthetic polymers are illustrative of suitable carriers. The synergizicide-pheromone compositions may be applied as a bait in a variety of ways conventional in the art, such as upon an exposed surface or in an exposed solution, or incorporated into a wick or other substrate.

The ratio and absolute amounts of the pheromone and organophosphorous insecticide may vary and are selected to yield a synergistic attraction of the insects. Suitable ratios and amounts may be readily determined by the practitioner skilled in the art. It will be recognized that the amount of pheromone employed should be effective or sufficient to attract the target insect. The actual effective amount of the organophosphorous insecticide may vary with the specific insecticide used, the species of pest, environmental conditions such as temperature, humidity and wind conditions, and the type of vehicle or carrier employed. However, whichever vehicle or carrier is employed, the amount of organophosphorous insecticide employed should be sufficient to provide a release rate from the vehicle or carrier into the atmosphere of about 0.005-0.1 mg of insecticide per hour to achieve the desired synergizicidal effect. For example, using mineral oil as a carrier, the release rate of the insecticide is relatively fast and thus the amount of insecticide may be relatively low, between about 1–20% by weight of the mineral oil. In contrast, when using other vehicles such as paraffin, or vials covered with a rubber septum, the release rate is relatively slow, requiring a greater amount of insecticide.

The following examples are intended only to further illustrate the invention and are not intended to limit the scope of the invention which is defined by the claims.

EXAMPLE 1

*C. freemani* beetles were field collected in oak woods and corn fields near Bath, Ill., by attracting them to traps that were baited with fermenting whole wheat dough and fermenting banana. The beetles were then maintained in the laboratory on a pinto bean diet as described by Dowd [J. Econ. Entomol. 80: 1351–1353 (1987)]. The aggregation pheromone, (2E,4E,6E)-5-ethyl-3-methyl-2,4,6-nonatriene, for this species was synthesized as described by Bartelt et al. (supra). The insecticides listed in Table I were evaluated as synergizicides for the *C. freemani* pheromone by a wind-tunnel bioassay [Bartelt et al., supra]. The results of the evaluations are reported in Table I.

EXAMPLE 2

The procedures of Example 1 were repeated except that the beetles were of the *C. hemipterus* species, originally obtained from John Lussenhop (Department of Biology, University of Illinois, Chicago). Also, the aggregation pheromone for this species was isolated from male beetles by the procedure described by Bartelt et al. (supra), and the C-13 major component of the pheromone was (2E,4E,6E,8E)-3,5,7-trimethyl-2,4,6,8-decatetraene. The results of the evaluations are reported in Table II.

EXAMPLE 3

The procedures of Example 1 were repeated except that the beetles were of the *C. lugubris* species, and the insecticides were those listed in Table III. The aggregation pheromone, (2E,4E,6E,8E)-3,5-dimethyl-7-ethyl-2,4,6,8-undecatetraene, for this species was also synthesized according to the method of Bartelt et al. (supra). The results of the evaluations are reported in Table III.

It is understood that the foregoing detailed description is given merely by way of illustration and that modification and variations may be made therein without departing from the spirit and scope of the invention.

TABLE I

| | | Number of *C. freemani* attracted | | | | |
|---|---|---|---|---|---|---|
| Example | Insecticide | Insecticide | Pheromone | Insecticide + pheromone | Synergist ratio | Probability |
| 1A | Dichlorvos | 0.88 ± 0.61 | 10.1 ± 1.0 | 35.1 ± 8.0 | 3.19 | .011 |
| 1B | Thiometon | 0.17 ± 0.14 | 12.0 ± 1.3 | 28.5 ± 1.9 | 2.34 | .000 |
| 1C | Naled | 0.17 ± 0.14 | 5.7 ± 1.6 | 16.8 ± 4.2 | 2.85 | .013 |

Values for insecticides are means ± standard errors of eight solo tests (insecticide alone) in Example 1A and six solo tests in Examples 1B and 1C. Values for pheromones and pheromones + insecticide are means ± standard errors of eight paired comparisons (pheromone vs. pheromone + insecticide) in Example 1A and six paired comparisons in Examples 1B and 1C. The test volumes of both insecticides and pheromone were 20 microliter. The test volume of insecticide + pheromone was 40 microliter. Concentration of insecticides was 10% (by weight) in mineral oil; that of the pheromone was 2-3 ng/microliter in hexane. When tested in combination, the insecticide and pheromone were applied to different spots on paper, while Dichlorvos was released from a 40% impregnated plastic block, about 2 × 2 × 0.5 cm (Raid).

The synergist ratio is defined as the number of beetles attracted by the insecticide + pheromone divided by the sum of the beetles attracted by the insecticide and pheromone alone. Probability values are based on two-tailed paired t-tests of pheromone and insecticide + pheromone.

TABLE II

| | | Number of *C. hemipterus* attracted | | | | |
|---|---|---|---|---|---|---|
| Example | Insecticide | Insecticide | Pheromone | Insecticide + pheromone | Synergist ratio | Probability |
| 2A | Dichlorvos | 2.4 ± 1.4 | 17.5 ± 4.6 | 39.1 ± 8.9 | 1.96 | .003 |
| 2B | Thiometon | 1.4 ± 0.65 | 13.0 ± 5.5 | 31.0 ± 12.7 | 2.15 | .045 |

TABLE II-continued

| | | Number of C. hemipterus attracted | | | |
|---|---|---|---|---|---|
| Example | Insecticide | Insecticide | Pheromone | Insecticide + pheromone | Synergist ratio | Probability |
| 2C | Naled | 0.0 ± 0.0 | 11.6 ± 5.2 | 27.9 ± 11.8 | 2.41 | .052 |

Values for insecticides are means ± standard errors of five solo tests (insecticide alone) in Example 2A and eight solo tests in Examples 2B and C. Values for pheromones and pheromones + insecticides are means ± standard errors of eight paired tests (pheromone vs. pheromone + insecticide) in Example 2A and seven paired tests in Examples 2B and C. The test volumes of both insecticides and pheromone were 20 microliters. The test volume of insecticide + pheromone was 40 microliter. Concentration of insecticides was 10% (by weight) in mineral oil; that of the major component of the pheromone was about 2 ng total per test at a concentration of about 100 picogram/microliter in hexane. When applied together, the insecticide and pheromone were applied to different spots on paper, while Dichlorvos was released from a 40% impregnated plastic block, about 2 × 2 × 0.5 cm (Raid).
The synergist ratio is defined as the number of beetles attracted by the insecticide + pheromone divided by the sum of the beetles attracted by the insecticide and pheromone alone. Probability values are based on two-tailed paired t-tests of pheromone and insecticide + pheromone.

TABLE III

| | | Number of C. lugubris attracted | | | |
|---|---|---|---|---|---|
| Example | Insecticide | Insecticide | Pheromone | Insecticide + pheromone | Synergist ratio | Probability |
| 3A | Parathion | 2.0 | 47.1 | 80.4 | 1.64 | <.01 |
| 3B | IBP | 0.25 ± 0.24 | 24.1 ± 3.5 | 34.3 ± 5.6 | 1.41 | .011 |

Example 3A was conducted according to a balanced incomplete block design and the values are from seven blocks of four repetitions of each treatment. Values for insecticide in Example 3B are means ± standard errors of four solo tests (insecticide alone). Values for pheromones and pheromone + insecticides in Example 3B are means ± standard errors of 10 paired tests (pheromone vs. pheromone + insecticide). Concentrations, volumes, and application were the same as in Example 2.
The synergist ratio is defined as the number of beetles attracted by the insecticide + pheromone divided by the sum of the beetles attracted by the insecticide and pheromone alone. The probability in Example 3B is based on two-tailed paired t-tests of pheromone and insecticide + pheromone.

We claim:

1. A composition for attracting and killing nitidulid beetles comprising substantially pure pheromone attractant for said nitidulid beetles and an organophosphorus insecticide, wherein said pheromone comprises a hydrocarbon or mixtures of hydrocarbons having the structure:

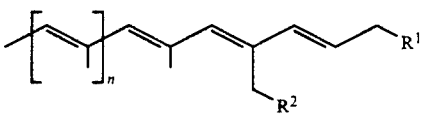

wherein $R^1$ and $R^2$ are independently selected from the group consisting of hydrogen and lower alkyl, and n is zero or one.

2. A composition as described in claim 1 wherein said organophosphorus insecticide is selected from the group consisting of dichlorovos, thiometon, naled, parathion, and IBP.

3. A composition as described in claim 1 wherein $R^1$ is hydrogen, $R^2$ is hydrogen, and n is one.

4. A composition as described in claim 1 wherein $R^1$ is methyl, $R^2$ is hydrogen, and n is one.

5. A composition as described in claim 1 wherein $R^1$ is hydrogen, $R^2$ is methyl, and n is one.

6. A composition as described in claim 1 wherein $R^1$ is methyl, $R^2$ is methyl, and n is one.

7. A composition as described in claim 1 wherein $R^1$ is ethyl, $R^2$ is hydrogen, and n is one.

8. A composition as described in claim 1 wherein $R^1$ is methyl, $R^2$ is methyl, and n is zero.

9. A composition as described in claim 1 wherein said pheromone is an isolate from male nitidulid beetles selected from the group consisting of Carpophilus freemani, C. hemipterus, and C. lugubris.

10. A method of attracting and killing nitidulid beetles comprising exposing said nitidulid beetles to a composition comprising substantially pure pheromone attractant for said nitidulid beetles and an organophosphorus insecticide, wherein said pheromone comprises a hydrocarbon or mixtures of hydrocarbons having the structure:

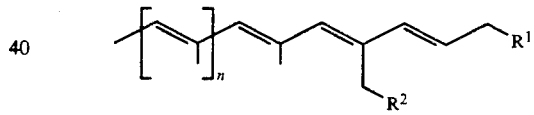

wherein $R^1$ and $R^2$ are independently selected from the group consisting of hydrogen and lower alkyl, and n is zero or one.

11. A method as described in claim 10 wherein said organophosphorus insecticide is selected from the group consisting of dichlorvos, thiometon, naled, parathion, and IBP.

12. A method as described in claim 10 wherein $R^1$ is hydrogen, $R^2$ is hydrogen, and n is one.

13. A method as described in claim 10 wherein $R^1$ is methyl, $R^2$ is hydrogen, and n is one.

14. A method as described in claim 10 wherein $R^1$ is hydrogen, $R^2$ is methyl, and n is one.

15. A method as described in claim 10 wherein $R^1$ is methyl, $R^2$ is methyl, and n is one.

16. A method as described in claim 10 wherein $R^1$ is ethyl, $R^2$ is hydrogen, and n is one.

17. A method as described in claim 10 wherein $R^1$ is methyl, $R^2$ is methyl, and n is zero.

18. A method as described in claim 10 wherein said beetles are Carpophilus freemani beetles and said pheromone is an isolate from male C. freemani beetles.

19. A method as described in claim 10 wherein said beetles are C. hemipterus beetles and said pheromone is an isolate from male C. hemipterus beetles.

20. A method as described in claim 10 wherein said beetles are *C. lugubris* beetles and said pheromone is an isolate from male *C. lugubris* beetles.

21. A composition as described in claim 1 wherein the amount of said organophosphorus insecticide is effective to provide a release rate from the composition into the atmosphere of about 0.005–0.1 mg of said insecticide per hour.

22. A method as described in claim 11 wherein the amount of said organophosphorus insecticide is effective to provide a release rate from the composition into the atmosphere of about 0.005–0.1 mg of said insecticide per hour.

* * * * *